United States Patent [19]
Coates et al.

[11] 3,933,744
[45] Jan. 20, 1976

[54] ESTERS AND MIXTURES THEREOF WITH ORGANOTIN COMPOUNDS USEFUL AS POLYMER STABILIZERS

[75] Inventors: Harold Coates, Wombourne; John Desmond Collins, Albrighton; Iftikhar H. Siddiqui, Edgbaston, all of England

[73] Assignee: Albright & Wilson Limited, Oldbury near Birmingham, England

[22] Filed: June 16, 1975

[21] Appl. No.: 586,955

Related U.S. Application Data
[62] Division of Ser. No. 442,874, Feb. 15, 1974.

[30] Foreign Application Priority Data
Feb. 19, 1973 United Kingdom................ 7984/73

[52] U.S. Cl.................. 260/45.75 S; 260/45.75 J; 260/45.85 S; 260/470 R; 260/481 R
[51] Int. Cl.².............................................. C08J 3/20
[58] Field of Search . 260/45.75 S, 45.75 J, 45.85 S, 260/470 R, 481 R, 30.8 R

[56] References Cited
UNITED STATES PATENTS

| | | | |
|---|---|---|---|
| 2,530,872 | 11/1950 | Gregory et al.................. | 260/481 R |
| 2,980,729 | 4/1961 | Buret.............................. | 260/481 R |
| 3,217,004 | 11/1965 | Heckenkleikner................ | 260/429.7 |
| 3,494,947 | 2/1970 | Schutze et al. .................... | 260/481 |
| 3,845,017 | 10/1974 | Collins et al.................. | 260/45.75 S |
| 3,890,276 | 6/1975 | Stapfer......................... | 260/45.75 J |

*Primary Examiner*—V. P. Hoke
*Attorney, Agent, or Firm*—Robert P. Auber; Kenneth G. Wheeless; Robert Spector

[57] ABSTRACT

An ester, which is a costabiliser of mono ordi organotin stabilisers for halogen containing resins, is of formula

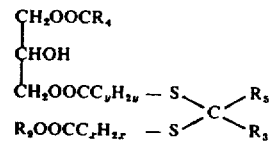

wherein $x$ and $y$ are 1–6, $R_4$ and $R_9$ are alkyl, alkenyl, cycloalkyl or optionally substituted aromatic aralkyl or aralkenyl hydrocarbyl group, $R_3$ and $R_5$ are as $R_4$ or $R_9$ or is hydrogen or $R_3$ and $R_5$ form a cycloalkyl ring. The organotin stabilisers are carboxylates, mercapto carboxylates, carboxylate ester from diacids, sulphides, mercaptides or thiostannoic acids.

21 Claims, No Drawings

ESTERS AND MIXTURES THEREOF WITH ORGANOTIN COMPOUNDS USEFUL AS POLYMER STABILIZERS

This is a divisional of application Ser. No. 442,874 filed Feb. 15, 1974.

The present invention relates to compounds, which act as costabilizers for organotin compounds in the stabilization of Halogen containing polymers such as polyvinyl chloride.

In the complete specification of our Copending British Application No. 55042/72 we have described organotin compounds of the general formula

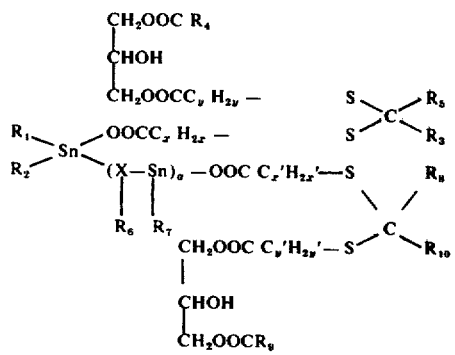

wherein
a is 0 or 1,
each of $x$, $x'$, $y$ and $y'$, which are the same or different, is an integer of 1 – 6
each of $R_1$, $R_2$, $R_6$ and $R_7$, which are the same or different is an alkyl group of 1 to 12 carbon atoms, a cycloalkyl group, an aromatic hydrocarbyl group or an aralkyl hydrocarbyl group,
each of $R_4$ and $R_9$, which are the same or different, is as defined above for $R_1$, $R_2$, $R_6$ and $R_7$, or is an alkyl group of 13–21 carbon atoms, an alkenyl group of 2 to 21 or an inertly substituted aromatic hydrocarbon group, each of $R_3$, $R_5$, $R_8$ and $R_{10}$, which are the same or different, is as defined above for $R_4$ and $R_9$, or is hydrogen or at least one of the pairs $R_3$ and $R_5$ and $R_8$ and $R_{10}$, together with the carbon atom to which they are attached, forms a cycloalkyl ring, and X is oxygen or sulphur.

These compounds are stabilizers for halogen containing resins.

wherein, each of $R_4$ and $R_9$, which are the same or different, is an alkyl group of 1 to 21 carbon atoms, an alkenyl group of 2–21 atoms, cycloalkyl group, aromatic hydrocarbyl group e.g. of 6 to 19 carbon atoms e.g. phenyl or aralkyl or aralkenyl hydrocarbyl group e.g. of 7 to 19 carbon atoms such as benzyl, orstyryl or an inertly substituted derivative of the aromatic, aralkyl or aralkenyl hydrocarbyl group, wherein the substituent is preferably at least one group of formula —OH, —OR$_4$, —SR$_4$, —COOR$_4$, —OOCR$_4$ or —SSR$_4$,
each of $R_3$ and $R_5$, which are the same or different, is as defined above for $R_4$ and $R_9$, or is hydrogen or $R_3$ and $R_5$ together with the carbon atom to which they are attached forms a cyclo alkyl ring, preferably a cyclohexane ring, and each of $x$ and $y$ which are the same or different, is an integer of 1 - 6.

$R_9$ is preferably an alkyl group of 4–18 carbon atoms e.g. 6–12 carbon atoms such as an iso n-octyl group, or cycloalkyl group of 5–8 carbon atoms e.g. cyclohexyl group. $R_5$ is preferably hydrogen or alkyl of 1 to 6 carbon atoms e.g. a methyl group. $R_4$ is preferably an alkyl or alkenyl group of 10 to 19 carbon atoms, preferably a linear one e.g. of formula $CH_3(CH_2)_z$ —, where z is an integer of 9–18, preferably 10–17 and especially 16. $R_3$ is preferably a phenyl, styryl or substituted phenyl (the substituents being for example alkyl of 1 to 6 carbon atoms especially methyl, or alkoxy of 1 to 6 carbon atoms, especially methoxy or hydroxy) group, branched chain alkyl group of 3–10, e.g. 4–8 carbon atoms, preferably that in which the free valency is at the point of branching i.e. of formula —CH $R_{11}$ $R_{12}$, where $R_{11}$ and $R_{12}$ are alkyl groups of 1 to 6 carbon atoms, especially ethyl and butyl, e.g. pent - 3 - yl and hept - 3 - yl groups or a straight chain alkyl group of 7 to 13 carbon atoms e.g. n-nonyl and n-undecyl group x and y are preferably 1 or 2. The groups $C_xH_{2x}$ and $C_yH_{2y}$ are preferably linear e.g. of formula $(CH_2)_x$.

In preferred compounds, the group

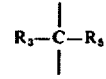

represent groups of formula

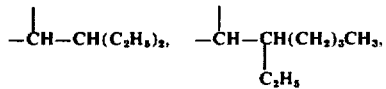

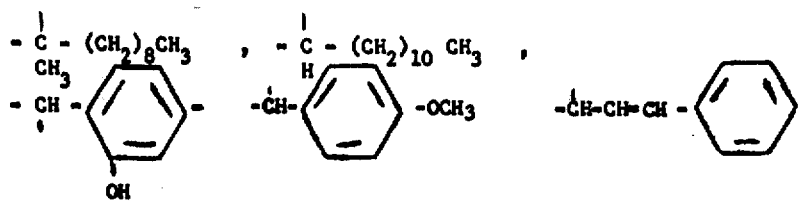

We have now found that ester derivatives of the tin free part of the above stabilizers can act as costabilizers for organotin compounds.

The present invention provides esters of the general formula

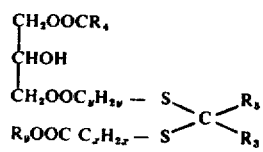

Preferred compounds are those of formula

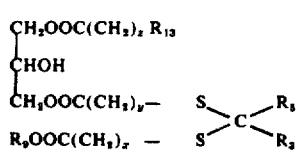

wherein each of $R_3$ and $R_{13}$, which are the same or different, is an alkyl group of 1 to 12 carbon atoms, a cycloalkyl group, an aryl or aralkyl group, $R_5$ is hydrogen, an alkyl or aryl group, $R_9$ is an alkyl group of 1 to 20 carbon atoms, a cycloalkyl group or an aryl or aralkyl group, $z$ is an integer of 1 to 20 and $x$ and $y$ are integers of 1 to 6. Preferably $R_{13}$ is a methyl group, $R_5$ is hydrogen or alkyl e.g. methyl group, $R_3$ is a phenyl or styryl group, a substituted phenyl group, a branched chain alkyl group of 4–8 carbon atoms or a straight chain alkyl group of 7 to 13 carbon atoms, $R_9$ is an alkyl or cycloalkyl group of 4 to 8 carbon atoms, $x$ and $y$ are 1 or 2 and $z$ is 10–16.

The present invention also provides a process for preparing the ester compounds, which comprises reacting substantially equimolar amounts of a glycerol ester of formula $R_4\ COOCH_2\ OOCC_yH_{2y}SH$ with a carbonyl compound of formula $R_3R_5CO$ and a mercapto ester of formula $R_9OOCC_xH_{2x}SH$. Alternatively, an acid of formula

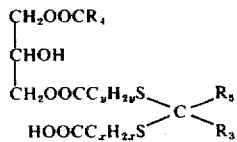

can be reacted by known methods with a hydroxylic compound of formula $R_9OH$ or a halide of formula $R_9Hal$ (when $R_9$ is an alkyl cycloalkyl or aralkyl group and Hal is chlorine, bromine or iodine), the reaction with the hydroxylic compound being preferably carried out in the presence of an acid catalyst, and the reaction with the halide being preferably carried out in the presence of a basic catalyst. The acid is preferably prepared by reacting substantially equimolar amounts of the glycerol ester with the carbonyl compound and a mercapto acid of formula $HOOCC_xH_{2x}SH$. Thus the ester compounds can be prepared by reacting substantially equimolar amounts of the glycerol ester with the carbonyl compound and a mercapto compound of formula $R_{18}OOCC_xH_{2x}SH$, where $R_{18}$ is $R_9$ or hydrogen, reacting the product with the hydroxylic compound or halide.

Preferably the glycerol ester is prepared in situ by reaction of substantially equimolar amounts of a compound of formula $R_4COOCH_2CHOHCH_2OH$ and a mercapto acid of formula $HOOC\ C_yH_{2y}SH$. The term "substantially equimolar amounts" means here not more than 30% molar excess of any reactant. The term "known methods" means methods heretofore used or described in the chemical literature.

Thus the compounds of the invention are generally prepared by the reaction of mono-ester of glycerol, such as glycerol mono-stearate, with a mercapto carboxylic acid such as thioglycollic acid or β-mercaptopropionic acid and subsequently admixing this with an aldehyde or ketone such as 2 - ethyl butyraldehyde, dodecylaldehyde, anisaldehyde, cinnamaldehyde or methyl nonyl ketone, and a mercapto-carboxylic ester such as iso-octyl thioglycollate or iso-octyl β - mercaptopropionate.

Frequently the reactions to form the ester compounds of the invention are carried out in the same solvent medium, which may be an aromatic hydrocarbon, e.g. benzene, toluene or xylene, an aliphatic hydrocarbon e.g. hexane or petroleum ether b.p. (80° or a cyclo-aliphatic hydrocarbon e.g. cyclohexane). It is often desirable (except in the reaction of the halide) to have an acidic catalyst present in the reaction, e.g. p-toluene sulphonic acid, hydrochloric acid or a metal chloride suitable as a Friedel Crafts catalyst, such as zinc chloride.

The esters of the invention are costabilizers with organotin compounds for halogen containing resins. The present invention also provides stabilizer compositions comprising an ester of the invention and an organotin compound of formula

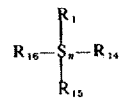

wherein $R_1$ represents an alkyl group of 1–12 carbon atoms, preferably 4–8 carbon atoms e.g. butyl or octyl, a cycloalkyl group preferably of 5–8 carbon atoms e.g. a cyclohexyl group, an aromatic hydrocarbyl group e.g. of 6–19 carbon atoms e.g. phenyl or aralkyl hydrocarbyl group e.g. of 7–19 carbon atoms such as benzyl, $R_{14}$ is as defined for $R_1$ or each of $R_{14}$, $R_{15}$ and $R_{16}$, which are the same or different is of formula $-OOCR_4$, $-OOCR_{17}COOR_9$, $-SC_xH_{2x}\ COOR_9$ or $-SR_4$, or $R_{15}$ and $R_{16}$ together represent $-S-$, $-OOCR_{17}COO-$, $-SC_xH_{2x}COO-$ or $R_{15}$ and $R_{16}$ together represent $-S-$ and $R_{14}$ represents $-SH$, wherein $R_4$ is as defined above, preferably an alkyl group of 8–18 carbon atoms, especially 11 or 12 carbon atoms, $x$ is as defined above, and is preferably 1 or 2, and $R_{17}$ is an alkylene group e.g. of 1 to 10 carbon atoms, an alkenylene group e.g. of 2 to 10 carbon atoms a cycloalkylene group e.g. of 5 to 7 carbon atoms such as cyclohexylene group or an arylene group, preferably a divalent aromatic hydrocarbyl group e.g. of 6 to 18 carbon atoms such as phenylene.

For example the organotin compound may be a mono or di organotin carboxylate of formula $R_1\ (R_{14})\ Sn(OOCR_4)_2$ where $R_{14}$ represents $R_1$ or $OOCR_4$, e.g. dibutyltin dilaurate or dioctyltin dilaurate. The organotin compound may be a mono or di organo carboxylate from a dicarboxylic acid or a half ester thereof, i.e. of formula $R_1\ (R_{14})Sn(OOCR_{17}COOR_9)_2$ where $R_{14}$ represents $R_1$ or $-OOCR_{17}COOR_9$ or $(R_1)_2Sn(OOCR_1\text{-}COO)$ e.g. where $R_{17}$ is an alkylene group of 1 to 6 carbon atoms e.g. 1,2 ethylene or an alkenylene group of 2–6 carbon atoms, preferably $-CH = CH-$ and where $R_9$ is e.g. an iso octyl group; examples of these carboxylates are di butyltin — and di octyltin — maleates, and di butyltin — and di octyltin — bis (iso octylmaleate), and the corresponding mono alkyltin tris compounds. The organotin compound may be a sulphide, a mercaptide or thio stannoic acid or thio stannoic acid ester, of formula $R_1Sn\ (=S)\ SH$, $R_1Sn\ (=S)\ SR_4$, $R_1\ (R_{14})\ Sn\ (SR_4)_2\ (R_1)_2SnS$ where $R_{14}$ represents $R_1$ or $SR_4$, and $R_4$ preferably represents an alkyl group of 8–18 carbon atoms e.g. of 12 carbon atoms; examples of such compounds are dibutyltin - sulphide and - bis (lauryl mercaptide), di octyltin - sulphide and - bis (lauryl mercaptide) and butyltin - and octyltin - thio stannoic acids and lauryl esters thereof.

Preferably the organotin compounds are mercapto carboxylate esters of formula $R_1\ (R_{14})\ SN\ (-S\ (CH_2)_x COOR_9)_2$ wherein $R_{14}$ represents $R_1$ or $-S(CH_2)_xCOOR_9$, or cyclic esters of formula $(R_1)_2Sn(-S(CH_2)_xCOO-)$, wherein $x$ is 1 or 2 and $R_9$ is an alkyl group of 6 to 18, preferably 6–12 carbon atoms, especially an iso octyl group; examples of such compounds are di butyltin - and di octyltin - bis (iso octyl thio glycollates), and di butyltin - and di octyltin - bis (iso octyl β - mercaptopropionates), and the corresponding mono alkyltin tris mercaptocarboxylates, and butyl and octyl tin cyclic thioglycollates and β-mercaptoproprionates.

The esters of the invention and organotin compounds are preferably present in the stabilizer compositions in a weight ratio of 0.1:1 to 1.5:1, preferably 0.2:1 to 1:1, especially 0.3:1 to 0.8:1.

The present invention also provides polymeric materials comprising a halogen containing resin and, as stabilizer therefor a stabilizer composition of the invention, usually in an amount of 0.1 to 10% by weight, preferably 1 to 8%, especially 1.1 to 6% (based on the weight of the resin). Typically the material contains 1–3% by weight of organotin compound and 0.1–3% by weight of ester (based on the weight of the resin).

The resin normally contains at least 40% by weight of chlorine. Usually it will be a polymer or co-polymer of vinyl chloride or vinylidene chloride but post-halogenated polyvinyl chloride or post-halogenated polyolefines, such as polyethylene, e.g. post chlorinated compounds, may be employed if desired. Suitable monomers which may form such copolymers with vinyl chloride and vinylidene chloride include for example acrylonitrile, vinyl acetate, methyl methacrylate, diesters of fumaric acid and maleic acid, ethylene, propylene and lauryl vinyl ether and these co-monomers may be present in an amount of up to 25% of the total weight of monomers co-polymerised.

Optionally, but advantageously, compositions according to the invention also contain hindered phenols, that is those having at least one alkyl substituent in a position ortho to the hydroxyl group, as auxiliary stabilizers. Such phenols preferably have 1–8 carbon atoms in each alkyl group, which is especially a tertiary butyl group. Examples of such phenols include butylated hydroxy-anisole, 2,6-di-tert.-butylphenol, methylene bis-(2,4-di-tert.-butylphenol), methylene bis-(2,6-di-tert.butylphenol), methylene bis-(2,6-di-tert.-butyl-3-methylphenol), 4,4'-butylidene bis-(6-tert.-butyl-3-methylphenol), methylene bis-(4-ethyl-6-tert.-butylphenol), methylene bis-(4-methyl-2,6-di-tert.-butylphenol). Particularly preferred, however, is 2,6-di-tert.-butyl-4-methyl-phenol.

Such phenols may be present in an amount of up to 3% preferably from 0.01 to 0.5% by weight of the resin and will normally be present at about 4–10% by weight, preferably 5–8% based on the total amount or organotin compounds used.

Esters of phosphorous and thiophosphorous acid may be employed in compositions according to the invention. Such compounds include halophosphites such as tris chloropropyl phosphite and polymeric phosphites such as those from hydrogenated 4,4'-isopropylidene diphenol. Preferred phosphites and thiophosphites, however, are monomers having no substituents in the organo-group and having no more than one sulphur atom. These include triaryl phosphites and trialkyl phosphites. Such compounds include, for example, triphenyl phosphite, trixylyl phosphite, trinonyl phenyl phosphite and trioctyl phosphite. Diesters of phosphorous acid such as di-isopropyl phosphite, dibutyl phosphite and diphenyl phosphite are also of use. Particularly preferred, however, are the mixed alkyl aryl phosphites such as octyl diphenyl phosphite, isodecyl diphenyl phosphite and di-isodecyl phenyl phosphite.

This particularly pronounced effect may also be obtained by employing a mixture of a triaryl phosphite and an alcohol in conjunction with the organotin compound. A particularly suitable mixture is that of triphenyl phosphite and isodecanol.

The stabilizer composition of the invention can also contain an epoxy compound, as may be desired for example in cases where a delay of initial colour change of the polymer is desired. Epoxy compounds which may be employed in such compositions include butyl epoxy stearate, esters of epoxidised oleic acid and compounds of the formula

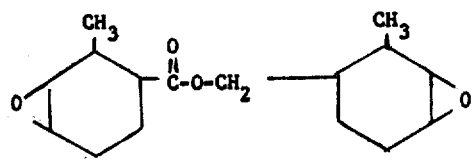

The stabilizer compositions as described above, optionally including a hindered phenol, an alkyl aryl phosphite or aryl phosphite or an epoxide, will often be used as the only stabilizer in a polymeric vinyl chloride or vinylidene chloride composition. However, if desired conventional thermal stabilizers may also be included. These may include, for example, metal soap stabilizers, such as cadmium, barium, or zinc salts of fatty acids, or lead salts such as lead carbonate or stearate or dibasic lead phosphite or phthalate, or tribasic lead sulphate.

In the practice of the invention the stabilizer composition may be mixed with the resin in the conventional manner for example by milling with the resin on heated rolls at 100°–160°C e.g. about 150°C, although higher temperatures may be used when convenient, or by being mixed with particles of the polymer and then melting and extruding the mixture or by adding the stabilizer to a liquid resin.

The organotin stabilizer formulation may be employed in either plasticized resin compositions, for example those plasticized with carboxylic ester plasticizers e.g. di-2-ethylhexyl phthalate, dibutyl sebacate or diiso octyl phthalate or with phosphate esters such as tri(alkyl phenyl) phosphates or may be employed in rigid compositions. Such rigid compositions contain little or no plasticizers although for some applications up to about 10% by weight of plasticizer may be present. This is in contrast with plasticized compositions where the amount of plasticizers present is normally greater than 50% by weight of the polymeric material and is often greater than 100% on that basis; amounts of 30–150% are often used.

In addition to the stabilizers, the compositions of the invention may also contain conventional additives e.g. pigments, fillers, dyes and ultraviolet absorbing agents.

The invention is illustrated in the following Examples:

EXAMPLE 1

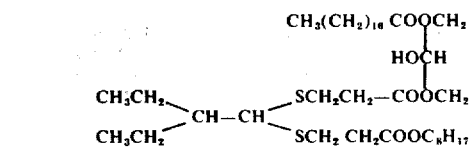

Glycerol mono stearate (34.8g, 0.1M) and β mercaptopropionic acid (10.6g, 0.1M) were refluxed in toluene (250 ml) in the presence of p-toluene sulphonic acid (0.2g) till the calculated amount of water had collected (to give $C_{17}H_{35}COOCH_2$ —CH(OH)—CH$_2$OOC CH$_2$ CH$_2$SH).

2 - ethyl butyraldehyde (10.0g, 0.1M) and iso - octyl β-mercaptopropionate (21.8g, 0.1M) were also added into the above warm solution and the mixture refluxed until the calculated amount of water had collected again. The hot solution was then rapidly filtered under partial vacuum and finally the toluene was removed from the warm solution under reduced pressure.

The product is a white soft waxy solid at room temperature.

| Analysis | |
|---|---|
| Calculated | Found |
| S = 8.57% | S = 8.6% |
| H = 10.4% | H = 10.43% |

Its structure was also confirmed by I.R. and N.M.R. analysis.

EXAMPLE 2

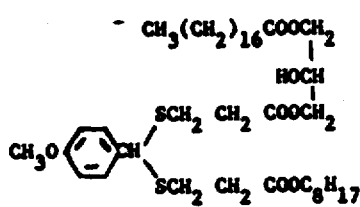

This compound was prepared by the same method as in Example 1 using the following quantities:

| Step (1) | (a) | Glycerol mono stearate | 34.8 g |
|---|---|---|---|
| | (b) | β-mercaptopropionic acid | 10.6 g |
| | (c) | p - toluene sulphonic acid | 0.3 g |
| | (d) | Toluene | 300 ml |
| Step (2) | (e) | Anisaldehyde | 13.6 g |
| | (f) | iso-octyl β-mercaptopropionate acid | 21.8 g |

The product is a slightly yellow soft waxy solid at room temperature. Its structure was confirmed by I.R. and N.M.R. analysis.

EXAMPLE 3

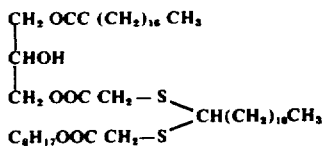

This compound was prepared by the same method as in Example 1 using the following quantities:

| Step (1) | | |
|---|---|---|
| (a) | Glycerol mono stearate | 34.8 gms |
| (b) | Thioglycollic acid | 9.2 gms |
| (c) | p-toluene sulphonic acid | 0.2 gms |
| (d) | Toluene | 300 ml |
| Step (2) | | |
| (e) | Dodecylaldehyde | 18.4 gms |
| (f) | iso-octyl thioglycollate | 20.4 gms |

The product is white soft waxy solid at room temperature.

| Analysis | |
|---|---|
| Calculated | Found |
| S = 7.2 | S = 7.7 |
| H = 10.0% | H = 10.8% |

Its structure was confirmed by I.R. and N.M.R. analysis.

EXAMPLE 4

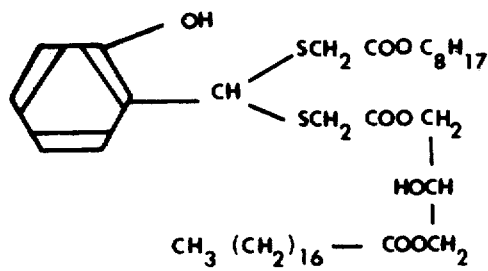

Salicylaldehyde (10.2g, 0.1M), iso-octyl thioglycollate (20.4g, 0.1M) and thioglycollic acid (9.2g, 0.1M) were refluxed in toluene (250ml) in the presence of p-toluene sulphonic acid (0.2g) till the calculated amount of water had collected (to give

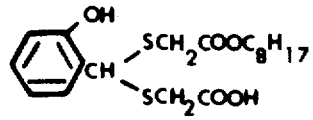

Glycerol mono stearate (34.8g, 0.1M) was also added into the above warm solution and the mixture refluxed until the calculated amount of water had collected again. The hot solution was filtered as in Example 1 and finally the toluene was removed from the warm solution under reduced pressure.

The product is a soft slightly yellow waxy solid at room temperature.

| Analysis | |
|---|---|
| Calculated | Found |
| S% = 8.6 | S% = 8.1 |
| H% = 9.2 | H% = 9.73 |
| C% = 64.9 Carbon | % = 65.9 |

EXAMPLE 5

The tin free compounds of Examples 1–4 of the present invention were tested as costabilizers with known organotin stabilizers for initial colour development of polyvinyl chloride on heating in comparison with the same organotin stabilizers without the tin free compounds.

300g samples of Rigid PVC compositions were made up as follows:

a. Polyvinyl chloride sold under the trade name Corvic D55/09 . . . . 100 parts b. Lubricant mixture of cetyl alcohol and stearyl alcohol sold under the trade name Plastilube 30 . . . . 0.5 parts present if marked * in following Table In many instances of the present invention the lubricant has not been added to the polymer because many of the compounds tested themselves act as a lubricant during milling at about 155°C.

c. Organotin Stabilizer 1 to 2 parts as shown in the Table.

Stabilizer x in the Table is dibutyltin bis (iso-octyl thioglycollate) and stabilizer y is dioctyltin bis (iso-octyl thioglycollate).

d. Tin-free compounds 0 – 1.5 parts as shown in the Table.

The following Table gives details of the various PVC compositions and the colour produced on heating them at 190°C.

which are the same or different, is as defined above for $R_4$ and $R_9$, or is hydrogen or $R_3$ and $R_5$, together with the carbon atom to which they are attached, forms a cycloalkyl ring.

2. An ester according to claim 1 wherein each of $x$ and $y$ is 1 or 2.

3. An ester according to claim 1 wherein $R_5$ is hydrogen or an alkyl group of 1–6 carbon atoms.

4. An ester according to claim 1 wherein $R_4$ is an alkyl group of 10–19 carbon atoms or an alkenyl group of 10–19 carbon atoms.

5. An ester according to claim 4 wherein $R_4$ is a group of formula $-(CH_2)_z - CH_3$ wherein $z$ is an integer of 10–16 carbon atoms.

TABLE

| Example | Tin Free Compound of Example No. | Parts by wt. per 100 parts of Polymer | Stabilizer | Parts by wt. per 100 parts of Polymer | Colour on Gardner Scale after heating at 190°C for given time in mins. | | | | | | |
|---|---|---|---|---|---|---|---|---|---|---|---|
| | | | | | 0 | 3 | 5 | 6 | 7½ | 9 | 10 | 12½ |
| Comparative | | NIL | x | 1.33* | 0 | — | 1–2 | — | — | — | 4–5 | — |
| 6 | 1 | 0.26 | x | 1.33 | 0 | — | 0 | — | — | — | 1–2 | — |
| 7 | 1 | 0.53 | x | 1.33 | 0 | — | 0 | — | — | — | 1–2 | — |
| 8 | 1 | 0.80 | x | 1.33 | 0 | — | 0 | — | — | — | 1–2 | — |
| 9 | 1 | 1.00 | x | 1.33 | 0 | — | 0 | — | — | — | 1 | — |
| 10 | 1 | 1.33 | x | 1.33 | 0 | — | 0 | — | — | — | 1+ | — |
| Comparative | | NIL | y | 1.33* | 2 | — | 3 | — | 6 | — | 6 | 7 |
| 11 | 1 | 0.53 | y | 1.33 | 0 | — | 0 | — | 1 | — | 2 | 3 |
| 12 | 1 | 0.80 | y | 1.33 | 0 | — | 0 | — | 0–1 | — | 2 | 3 |
| 13 | 1 | 1.00 | y | 1.33 | 0 | — | 0 | — | 1 | — | 2 | 3 |
| Comparative | | NIL | x | 1.33* | 0 | 0 | — | 3 | — | 4–5 | — | — |
| 14 | 2 | 0.53 | x | 1.33 | 0 | 0 | — | 0 | — | 3 | — | — |
| Comparative | | NIL | y | 1.33* | 3 | 3 | — | 4–5 | — | — | — | — |
| 15 | 2 | 0.53 | y | 1.33 | 0 | 1 | — | 2 | — | — | — | — |
| Comparative | | NIL | x | 1.33* | 0 | — | 2–3 | — | 3–4 | — | — | — |
| 16 | 3 | 0.53 | x | 1.33 | 0 | — | 0 | — | 3 | — | — | — |
| Comparative | | NIL | y | 1.33* | 3 | — | 3–4 | — | 4 | — | — | — |
| 17 | 3 | 0.53 | y | 1.33 | 0 | — | 1 | — | 3–4 | — | — | — |
| Comparative | | NIL | x | 1.5* | 0 | 0 | — | 2 | — | 4 | — | — |
| 18 | 4 | 0.6 | x | 1.5 | 0 | 0 | — | 0–1 | — | 2 | — | — |
| Comparative | | NIL | y | 1.5* | 2 | 2 | — | 3+ | — | 4–5 | — | — |
| 19 | 4 | 0.6 | y | 1.5 | 0 | 0 | — | 1– | — | 2– | — | — |

We claim:

1. An ester of the general formula

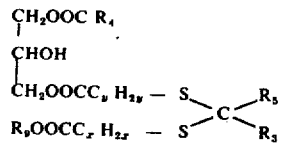

wherein,
each of x and y, which are the same or different, is an integer of 1–6
each of $R_4$ and $R_9$, which are the same or different, is selected from the group consisting of alkyl groups of 1 to 21 carbon atoms, alkenyl groups of 2–21 carbon atoms, cycloalkyl groups, aromatic hydrocarbyl groups, aralkyl hydrocarbyl groups and aralkenyl hydrocarbyl groups, each of $R_3$ and $R_5$, 6. An ester according to claim 1 wherein $R_3$ is selected from the group consisting of phenyl and styryl groups; substituted phenyl groups with at least one substituent, which is selected from the group consisting of alkyl groups of 1 to 6 carbon atoms, alkoxy groups of 1 to 6 carbon atoms and a hydroxy group; a branched chain alkyl group of 3–10 carbon atoms and a straight chain alkyl group of 7 to 13 carbon atoms.

7. An ester according to claim 6 wherein the branched chain alkyl group for $R_3$ is of formula — $CH(R_{11})R_{12}$ wherein each of $R_{11}$ and $R_{12}$, which are the same or different is an alkyl group of 1 to 6 carbon atoms.

8. An ester according to claim 6 wherein the group

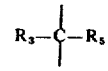

represents a group of formula

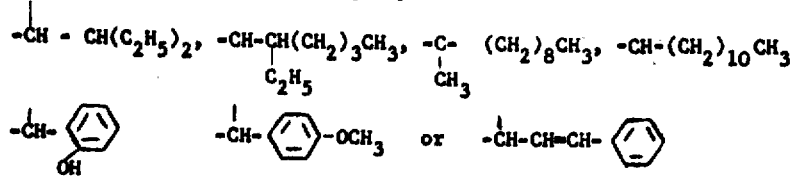

9. An ester according to claim 1 wherein $R_9$ is an alkyl group of 4–18 carbon atoms.

10. An ester according to claim 1 of the general formula

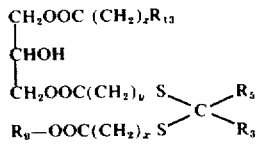

wherein each of $R_3$ and $R_{13}$, which are the same or different, is selected from the group consisting of alkyl groups of 1 to 12 carbon atoms, cycloalkyl groups, aryl and aralkyl groups, $R_5$ is selected from the group consisting of hydrogen, alkyl and aryl groups, $R_9$ is selected from the group consisting of alkyl groups of 1 to 20 carbon atoms, cycloalkyl groups and aryl and aralkyl groups, $z$ is an integer of 1 to 20 and $x$ and $y$ are integers of 1 to 6.

11. An ester according to claim 10 wherein the group

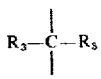

represents a group of formula — $CH(C_2H_5)_2$,

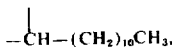

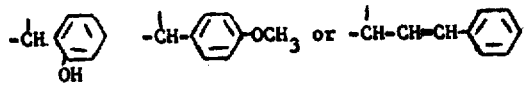

12. An ester according to claim 1 of the formula

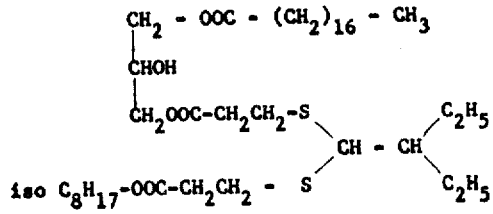

13. An ester according to claim 1 of the formula

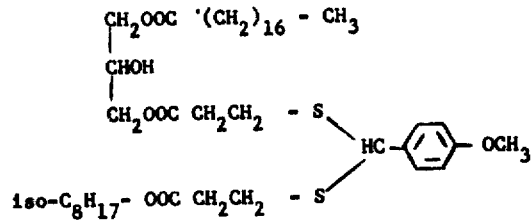

14. An ester according to claim 1 of the formula

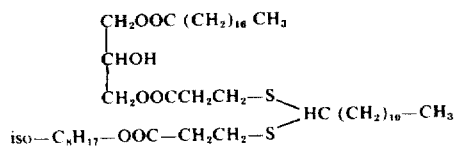

15. An ester according to claim 1 of the formula

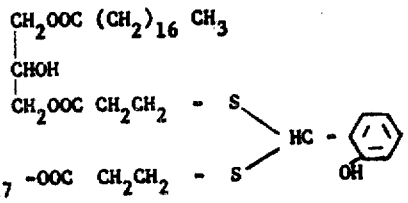

16. A process for preparing an ester as claimed in claim 1 which comprises reacting substantially equimolar amounts of a glycerol ester of formula $R_4COOCH_2\text{-}CHOH\ CH_2OOCC_yH_{2y}SH$ with a carbonyl compound of formula $R_3R_5CO$ and a mercapto ester of formula $R_9OOCC_xH_{2x}SH$, wherein $R_3$, $R_4$, $R_5$, $R_9$, $x$ and $y$ are as defined in claim 1.

17. A process for preparing an ester as claimed in claim 1, which comprises reacting an acid of formula

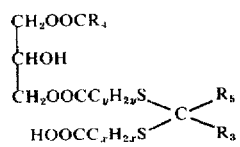

with a reactant selected from the group consisting of hydroxylic compounds of formula $R_9OH$ and halides of formula $R_9Hal$, wherein in the hydroxylic compound $R_9$ is as defined in claim 1 and in the halide $R_9$ is selected from the group consisting of alkyl groups of 1 to 21 carbon atoms, cycloalkyl groups and aralkyl hydrocarbonyl groups and Hal is selected from the group consisting of chlorine, bromine and iodine atoms, and $R_3$, $R_4$, $R_5$, $x$ and $y$ are as defined in claim 1.

18. A process according to claim 17 wherein the acid is prepared by reacting substantially equimolar amounts of a glycerol ester of formula $R_4COOCH_2\text{-}CHOHCH_2OOCC_yH_{2y}SH$ with the carbonyl compound of formula $R_3R_5CO$ and a mercapto acid of formula $HOOCC_xH_{2x}SH$.

19. A process according to claim 16 wherein the glycerol ester is prepared in situ by reaction of substantially equimolar amounts of a compound of formula $R_4COOCH_2\ CHOH\ CH_2\ OH$ and a mercapto acid of formula $HOOC\ C_yH_{2y}SH$.

20. A process according to claim 18 wherein the glycerol ester is prepared in situ by reaction of substantially equimolar amounts of a compound of formula $R_4COOCH_2\ CHOH\ CH_2\ OH$ and a mercapto acid of formula $HOOC\ C_yH_{2y}SH$.

21. A polymeric material which comprises a halogen-containing resin and, as stabilizer therefor a composition consisting of 1) an ester of the general formula

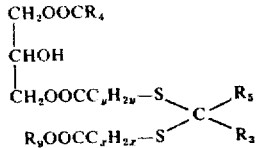

wherein each of $x$ and $y$, which are the same or different, is an integer of 1–6, each of $R_4$ and $R_9$, which are the same or different, is selected from the group consisting of alkyl groups of 1 to 21 carbon atoms, alkenyl groups of 2–21 carbon atoms, cycloalkyl groups, aromatic hydrocarbyl groups, aralkyl hydrocarbyl groups and aralkenyl hydrocarbyl groups, each of $R_3$ and $R_5$, which are the same or different, is as defined above for $R_4$ and $R_9$, or is hydrogen or $R_3$ and $R_5$, together with the carbon atom to which they are attached, forms a cycloalkyl ring, and 2) an organotin compound of the formula

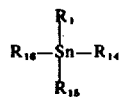

wherein $R_1$ is selected from the group consisting of alkyl groups of 1 to 12 carbon atoms, cycloalkyl groups, aromatic hydrocarbyl groups or aralkyl hydrocarbyl groups, $R_{14}$ is as defined for $R_1$ or each of $R_{14}$, $R_{15}$ and $R_{16}$, which are the same or different, is selected from the group consisting of groups of formula $-OOCR_4$, $-OOCR_{17}COOR_9$, $-SC_xH_{2x}COOR_9$ and $-SR_4$, or $R_{15}$ and $R_{16}$ together is selected from the group consisting of groups of formula $-S-$, $-OOCR_{17}COO-$, and $-SC_xH_{2x}COO-$, or $R_{15}$ and $R_{16}$ together represent $-S-$ and $R_{14}$ represents $-SH$, wherein $R_4$, $R_9$ and x are as defined in claim 1 and $R_{17}$ represents a group selected from the group consisting of alkylene, alkenylene, cycloalkylene and arylene groups.

* * * * *